(12) United States Patent
Hill et al.

(10) Patent No.: US 11,877,916 B2
(45) Date of Patent: Jan. 23, 2024

(54) PERINEAL THERAPY PAD

(71) Applicant: Parkview Health, Fort Wayne, IN (US)

(72) Inventors: John Hill, Monroeville, IN (US); Ashli J. Pershing, Wabash, IN (US); Pamela L Sprowl, Lafontaine, IN (US)

(73) Assignee: Parkview Health, Fort Wayne, IN (US)

( * ) Notice: Subject to any disclaimer, the term of this patent is extended or adjusted under 35 U.S.C. 154(b) by 737 days.

(21) Appl. No.: 16/864,265

(22) Filed: May 1, 2020

(65) Prior Publication Data

US 2020/0345561 A1 Nov. 5, 2020

Related U.S. Application Data (60) Provisional application No. 62/842,898, filed on May 3, 2019.

(51) Int. Cl.
| | | |
|---|---|---|
| *A61F 13/472* | (2006.01) | |
| *A61F 7/10* | (2006.01) | |
| *A61F 13/56* | (2006.01) | |
| *A61F 13/47* | (2006.01) | |
| *A61F 13/15* | (2006.01) | |

(52) U.S. Cl.
CPC ............. *A61F 13/472* (2013.01); *A61F 7/10* (2013.01); *A61F 13/5611* (2013.01); *A61F 2013/1517* (2013.01); *A61F 2013/4706* (2013.01)

(58) Field of Classification Search
CPC .. A61F 2013/15008; A61F 2013/49068; A61F 13/472; A61F 13/5611; A61F 7/10; A61F 2013/49077; A61F 2013/4706; A61F 13/476; A61F 13/5605; A61F 7/08
See application file for complete search history.

(56) References Cited

U.S. PATENT DOCUMENTS

| | | | |
|---|---|---|---|
| 3,175,558 A | | 6/1965 | Cailonette et al. |
| 3,474,780 A | * | 10/1969 | Fuchs ........................ A61F 5/30 128/95.1 |
| 3,809,096 A | * | 5/1974 | York ......................... A61F 7/10 607/108 |

(Continued)

FOREIGN PATENT DOCUMENTS

| | | | |
|---|---|---|---|
| CN | 2015-24173 | 7/2010 | |
| EP | 619953 A1 * | 10/1994 | ............... A41B 9/02 |
| WO | 2018/112501 | 6/2018 | |

*Primary Examiner* — Ophelia A Hawthorne (74) *Attorney, Agent, or Firm* — Faegre Drinker Biddle & Reath LLP (57) ABSTRACT

A body-contoured, T-shaped pad is designed to treat trauma to the perineal region of a new mother or other patient. The pad design may include specially designed T-shaped pad portions, an integrated ice pack, and relative positioning of the layers which combine to provide both cooling properties and proper absorption. For example, the pad includes an absorptive layer next to the skin, with an ice bag next to the absorptive layer which is designed to accept ice chips from commonly available ice machines found in hospital settings. The size and configuration of the pad assembly is designed for comfort, mobility, and compatibility with a patient's own undergarments. This design provides a cost-effective, single pad assembly which combines infection control with proper absorbency, provides high levels of patient comfort, and protects the dignity of the patient.

18 Claims, 6 Drawing Sheets

(56) References Cited

U.S. PATENT DOCUMENTS

| | | | |
|---|---|---|---|
| 3,867,939 | A | 2/1975 | Moore et al. |
| 4,240,436 | A | 12/1980 | Singleton |
| 5,062,425 | A | 11/1991 | Tucker |
| 5,167,655 | A | 12/1992 | McCoy |
| 6,248,125 | B1 | 6/2001 | Helming |
| 6,251,131 | B1 | 6/2001 | Kohout |
| 6,648,909 | B2 | 11/2003 | Helming |
| D537,161 | S | 2/2007 | Sinkiewicz |
| 7,425,171 | B2 | 9/2008 | Maupin |
| D667,129 | S | 9/2012 | Shelton |
| 8,273,367 | B2 | 9/2012 | Pesce et al. |
| 8,273,368 | B2 | 9/2012 | Ambrosio et al. |
| 8,937,212 | B2 | 1/2015 | Fogg et al. |
| 9,375,346 | B1 | 6/2016 | Sundheimer |
| D764,675 | S | 8/2016 | Peisner et al. |
| 9,572,709 | B2 | 2/2017 | Fogg |
| 10,035,016 | B2 | 7/2018 | Kolb et al. |
| 2005/0090796 | A1 | 4/2005 | Coleman et al. |
| 2006/0101558 | A1 | 5/2006 | Coleman et al. |
| 2008/0039810 | A1 | 2/2008 | Lee et al. |
| 2015/0282980 | A1 | 10/2015 | Ogunleye et al. |
| 2018/0289531 | A1 | 4/2018 | Thomas et al. |

\* cited by examiner

PERINEAL THERAPY PAD

CROSS-REFERENCE TO RELATED APPLICATION

This application claims the benefit under Title 35, U.S.C. § 119(e) of U.S. Provisional Patent Application Ser. No. 62/842,898, entitled PERINEAL THERAPY PAD and filed on May 3, 2019, the disclosure of which is expressly incorporated by reference herein in its entirety.

BACKGROUND

1. Technical Field

The present disclosure relates to pads used for cooling and absorption in injured areas, and, in particular, to therapy pads suitable for use for postpartum treatment or other treatment for trauma to the perineum and adjacent tissues.

2. Description of the Related Art

Pads for use is the perineal region of the body are known. Such pads may include provisions for absorbency, application of ice or other cold substances, or a combination of both. However, the existing standard of care in many neonatal units is for new mothers to wear three different pads simultaneously, in addition to the use of ice packs to control swelling.

In some patient settings, nurses have deconstructed and reassembled diapers or peri-pads to create improvised solutions for postpartum perineal therapy. The resulting devices were then mated to a traditional ice pack or cold pack to provide cooling to the perineum and adjacent areas, while also absorbing bleeding and other discharge. For example, two pads have been combined to create a "T" shaped construct with an intent to provide adequate coverage for bleeding. These improvised devices, while marginally effective, can lead patient concern about what appears to be excessive bleeding even though the fault is with the pad's inability to absorb and provide coverage. In addition, because such devices are mocked up by individual nurses from existing pads and ice packs (such as ice bags about 10 inches long and about 1.25 inches wide, which are commonly available in some hospital settings), these early efforts lack uniformity and may perform inadequately.

What is needed is an improvement over the foregoing.

SUMMARY

The present disclosure provides a body-contoured, T-shaped pad designed to treat trauma to the perineal region of a new mother or other patient. The pad design may include specially designed T-shaped pad portions, an integrated ice pack, and relative positioning of the layers which combine to provide both cooling properties and proper absorption. For example, the pad includes an absorptive layer next to the skin, with an ice bag next to the absorptive layer which is designed to accept ice chips from commonly available ice machines found in hospital settings. The size and configuration of the pad assembly is designed for comfort, mobility, and compatibility with a patient's own undergarments. This design provides a cost-effective, single pad assembly which combines infection control with proper absorbency, provides high levels of patient comfort, and protects the dignity of the patient.

In one embodiment, the present disclosure provides a perineal pad assembly including an inner cover configured to transport a bodily fluid away from the skin of a patient, an outer cover impermeable to the bodily fluid, and an ice pouch disposed between the perineal portion of the outer cover and the perineal portion of the inner cover. The inner cover and the outer cover cooperate to form a T-shape with a perineal portion extending along a ventral/dorsal direction and a dorsal portion extending along a medial/lateral direction.

In another embodiment, the present disclosure provides a perineal pad assembly including an inner cover configured to wick a bodily fluid, an outer cover impermeable to the bodily fluid, and an ice pouch disposed between the perineal portion of the outer cover and the perineal portion of the inner cover, the ice pouch including an opening disposed proximate a ventral edge of the of the perineal pad assembly, the opening sized to accept ice chips. The inner cover and the outer cover each form a T-shape with a perineal portion extending along a ventral/dorsal direction and a dorsal portion extending along a medial/lateral direction. The pad assembly further includes an absorbent body formed from a highly absorbent material and disposed between the ice pouch and the inner cover, the absorbent body forming a T-shape commensurate with the T-shape formed by the inner and outer covers.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. Although the exemplifications set out herein illustrate embodiments of the invention, in several forms, the embodiments disclosed below are not intended to be exhaustive or to be construed as limiting the scope of the invention to the precise forms disclosed.

DETAILED DESCRIPTION

Figure 1:
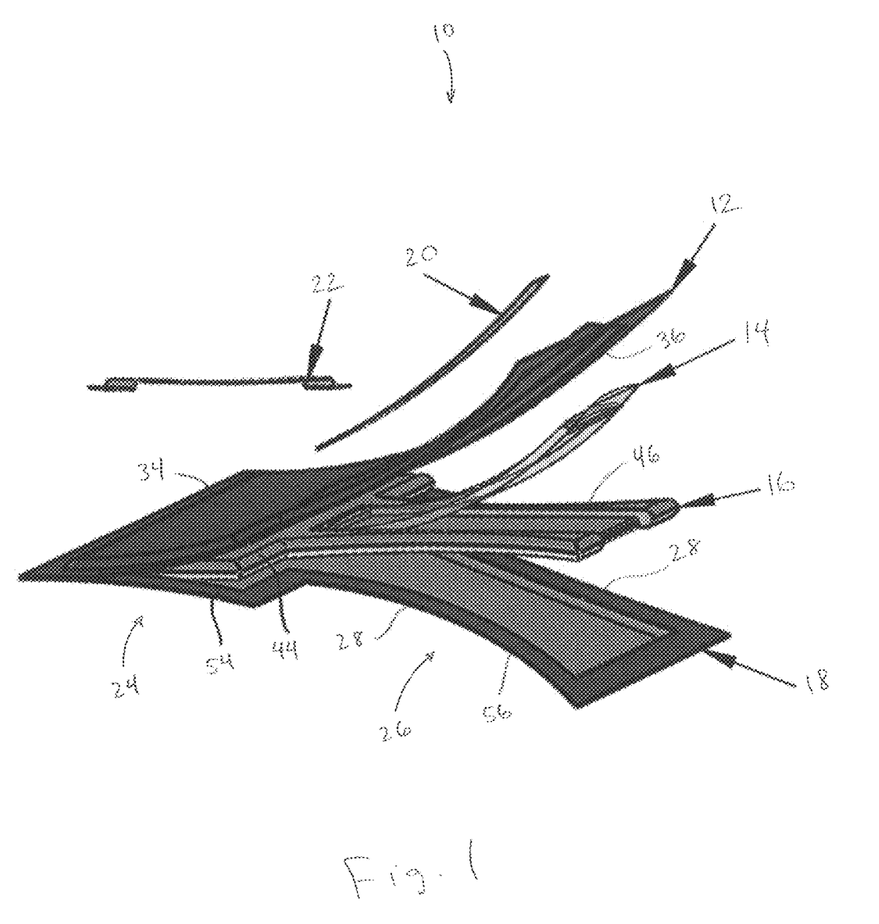
FIG. 1 is a perspective, exploded view of a pad assembly made in accordance with the present disclosure.

The present disclosure provides a T-shaped perineal pad assembly 10, shown in FIGS. 1-4, which includes a multi-layered structure to provide absorbency, cooling and fluid retention appropriate for patients with perineal trauma, such as new mothers. As shown in FIG. 1 and further described below, pad assembly 10 is formed as a multi-layer structure including an impermeable outer cover 12, an absorbent and/or wicking inner cover 18, and an ice pouch 14 and absorbent body 16 contained between the covers 12 and 18. These layers are configured and arranged to provide a simple, elegant and low-cost solution for the particular needs of a patient needing therapy in the perineal region, by combining cooling, fluid absorption and fluid retention into a single body-contoured construct.

FIGS. 2-6 illustrate pad assembly 10 in a flat configuration, as might be viewed from above when pad assembly 10 is lying on a flat surface. For purposes of the present disclosure, the various constructs and features of pad assembly 10 are described with reference to the intended application of the pad to the body of a patient. When so applied, a perineal portion 26 is applied to the perineum, and follows the natural contour of the body along a ventral/dorsal direction across the perineal region and extending approximately to the anus. Dorsal portion 24 extends from the dorsal end of the perineal portion 26 superiorly and dorsally along the buttocks to the top of the pubic bone and below the waistline.

Thus, pad assembly 10 is generally symmetrical about a sagittal plane of the body when applied, and crosses the frontal plane. The length L of perineal portion 26 (FIG. 4) extends along a generally ventral/dorsal direction, while the width W of dorsal portion 24 (FIGS. 4 and 5) extends along a generally medial/lateral direction.

Outer cover 12 is designed to retain bodily fluids during use of pad assembly 10. For example, outer cover 12 may be made of a watertight nonwoven or plastic material which inhibits or prevents seepage of fluid absorbed by absorbent layer 16 (shown in FIG. 1 and described further below) outwardly.

In addition, pad assembly 10 may include a peripheral strip 38 made from a nonwoven material extending around the entire periphery of outer cover 12. This peripheral strip 38 provides a relatively tight seal with the skin of the patient, inhibiting or avoiding leakage of bodily fluids outwardly. As also noted below, peripheral strip 38 may have a common width around its entire periphery to provide continuous and consistent skin contact around absorbent body 16. In one exemplary embodiment, this common width may be about 1-inch to provide for ample skin contact and a reliable seal against the skin.

Figure 3:
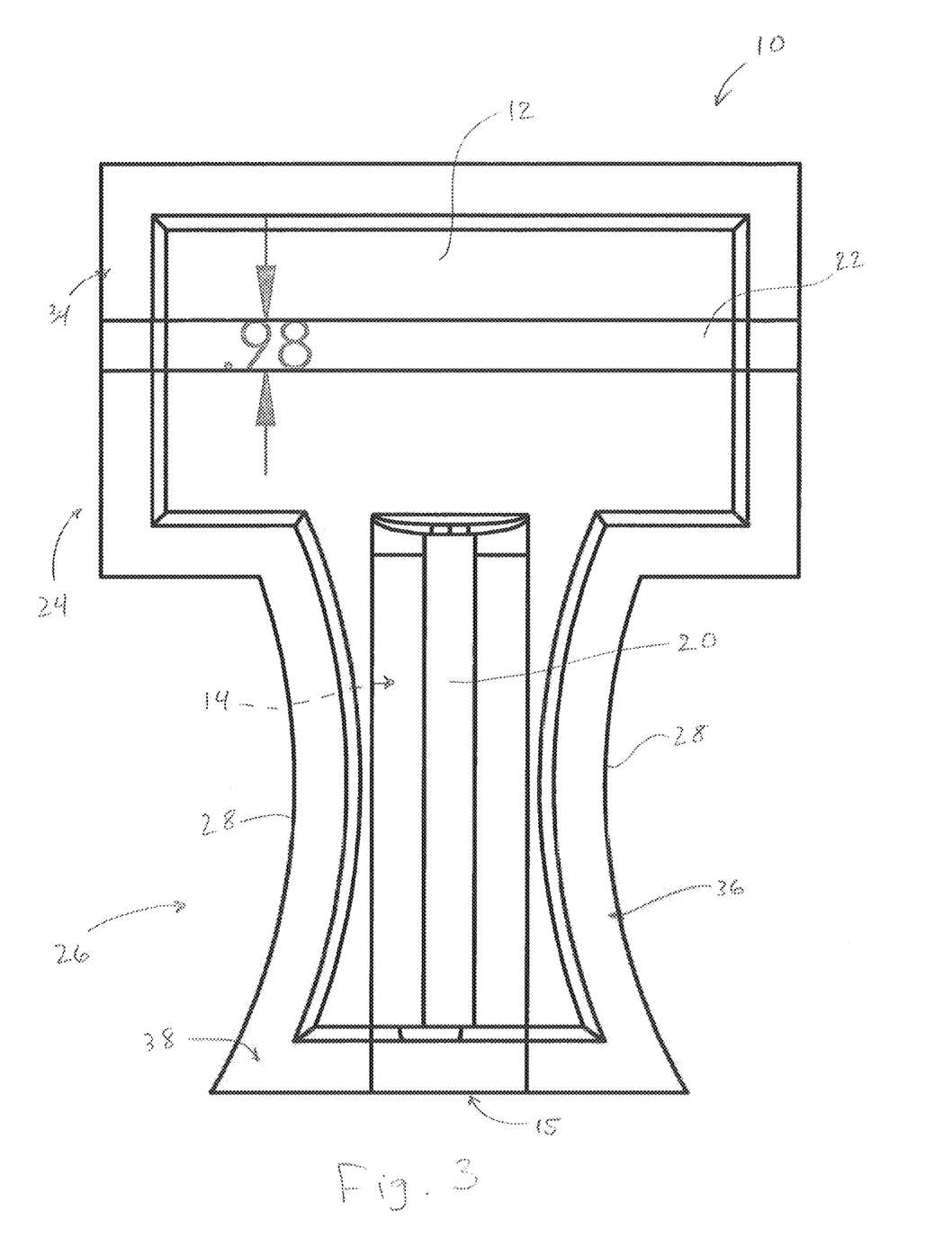
FIG. 3 is a top plan view of the pad assembly shown in FIG. 1.
Figure 4:
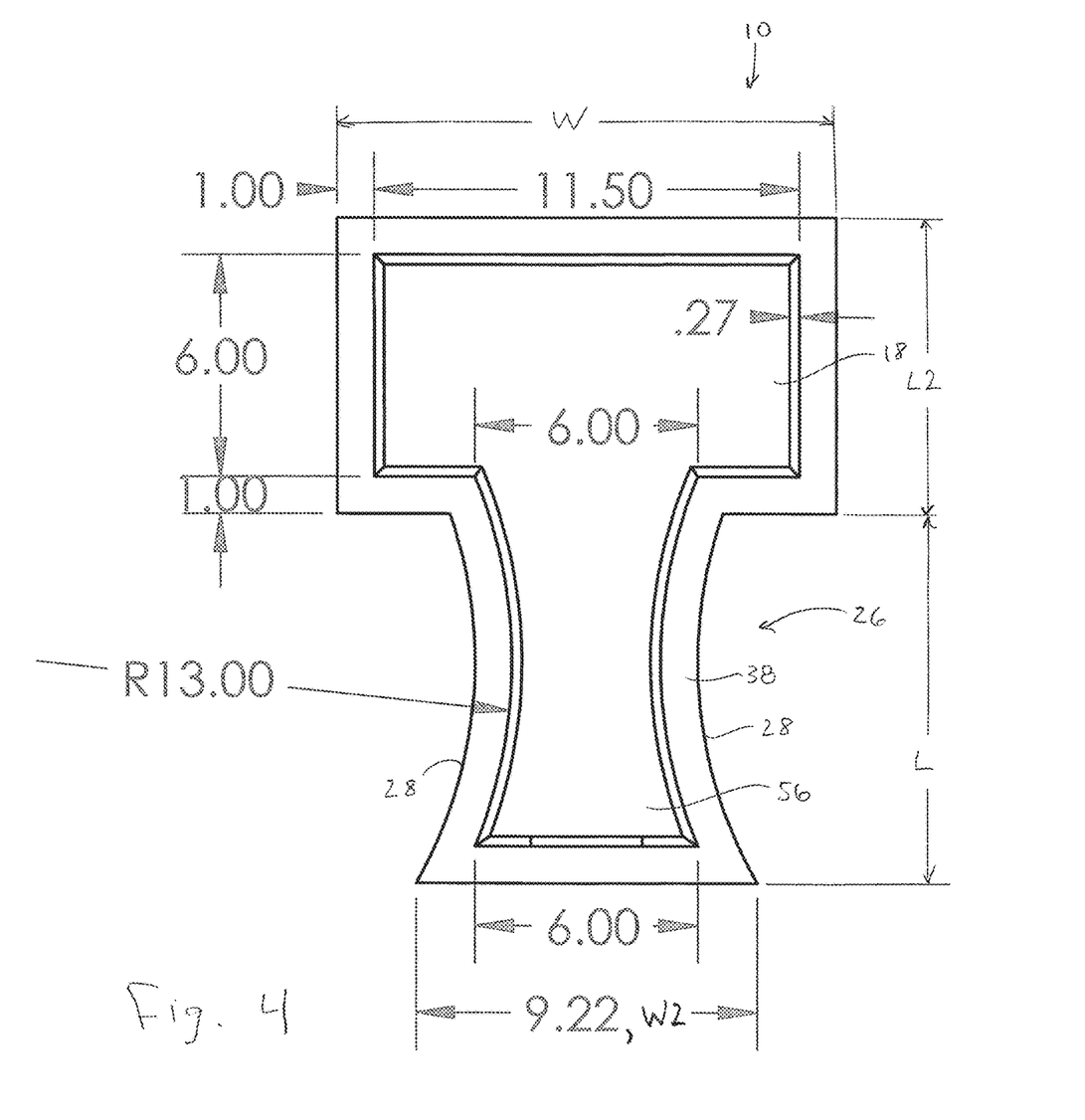
FIG. 4 is a bottom plan view of the pad assembly shown in FIG. 1.
Figure 5:
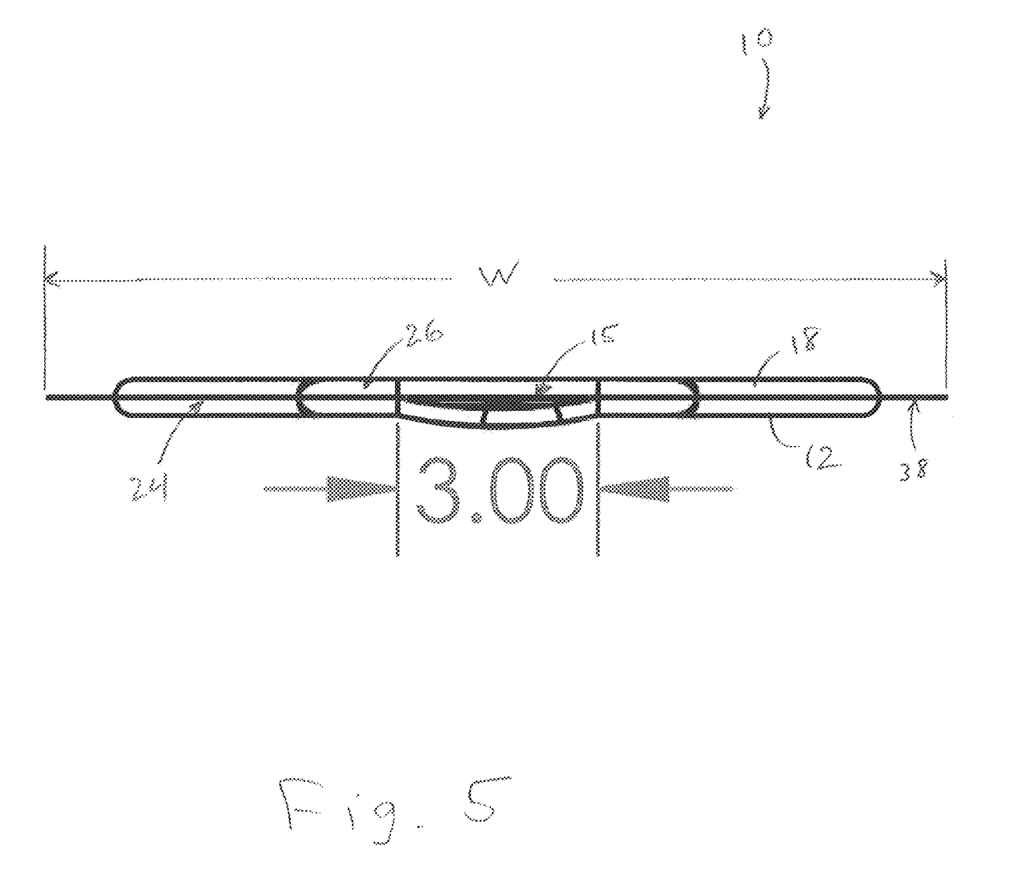
FIG. 5 is a front elevation view of the pad assembly shown in FIG. 1.

In the illustrated embodiment, peripheral strip 38 is integrally formed as a part of covers 12, 18 at the bonded junction therebetween. To facilitate this, outer cover 12 includes dorsal portion 34 and perineal portion 36 (FIGS. 1-3) which are the same size and shape as the corresponding dorsal portion 54 and perineal portion 56 of inner cover 18 (FIGS. 1 and 4). When bonded in this way, the dorsal portions 34, 54 cooperate to define the outer periphery of dorsal portion 24 of pad 10, while perineal portions 36, 56 cooperate to form the outer periphery of perineal portion 26 of pad 10. In an alternative construction, peripheral strip 38 may be formed as a separate construct bonded, glued or otherwise fixed to the exterior peripheries of outer and inner covers 12 and 18.

In contrast to the impermeable outer cover 12, inner cover 18 is designed to wick and/or absorb fluid when placed directly against the skin of the patient. In the illustrative embodiment of FIGS. 1 and 4, inner cover 18 wicks moisture and fluid away from the skin to absorbent body 16, which is made of a highly absorbent material capable of acting as a sponge to absorb and hold many times its weight in bodily fluid. As best seen in FIG. 1, absorbent body 16 includes dorsal portion 44 and perineal portion 46 which are commensurate in size and configuration to dorsal portions 34, 54 and perineal portions 36, 56 respectively. In particular, the outer periphery of absorbent body 16 is the same as the outer periphery of pad 10, except offset inwardly by the width of peripheral strip 38 (i.e., 1 inch in the illustrated embodiment).

As best seen in FIGS. 1-4, outer cover 12 and inner cover 18 cooperate to define the T-shaped outer profile of perineal pad 10. The proportions and nominal sizes associated with this T-shaped outer profile produce a shape that is specific to the contour of the perineal region of the human body and facilitate proper fit, function, comfort and dignity for the patient while also ensuring efficient production and low overall cost. FIG. 4, which is drawn to scale, shows dimensions in inches for one particular size of pad assembly 10. As illustrated, the width W of dorsal portion 24 (measured along the medial/lateral direction) is about 13.5 inches, while the length L of perineal portion 26 (measured along the ventral/dorsal direction) is about 10 inches, such that the ratio of width W to length L is 13.5:10 or 1.35. Similarly, the length L2 of dorsal portion 24 (ventral/dorsal) is about 8.0 inches and the width W2 of perineal portion 26 (medial/lateral) is about 9.22 inches (FIG. 4), for a ratio of width W2 to length L2 of 9.22:8.0 or 1.15. These ratios, both slightly over 1, quantify the "equilateral T-shape" of pad assembly 10 depicted in FIGS. 3 and 4. That is, the bottom part of the "T" (i.e., perineal portion 26) has about the same length as the width of the top part of the "T" (i.e., dorsal portion 24). This is reflected in the first ratio (W:L or 13.5:10), depicted as slightly above 1 at 1.35. In addition, both parts of the "T" also have similar extents perpendicular to their longitudinal direction. This is reflected in the second ratio (W2:L2 or 9.22:8.0), depicted as slightly above 1 at 1.15.

This "equilateral T-shape" provides a desired balance between perineal length and coverage, on one hand, and dorsal width and coverage, on the other. As noted herein, perineal portion 26 has an appropriate length and width for full but comfortable coverage of the perineum and adjacent areas, which ensures comprehensive absorption while preserving patient comfort and compatibility with existing undergarments. At the same time, dorsal portion 24 has a length and width that provides large-volume absorbency for a patient that is often supine during recovery, while avoiding protrusion above the waistline for compatibility with existing undergarments and partial or total concealment under clothing. These particular dimensions and ratios cooperate to provide pad assembly 10 which is highly absorbent and an effective moisture barrier, but also can be worn with and/or concealed under a patient's own clothing. Together, these features combine to protect patient dignity by allowing the patient to "feel normal" and minimally burdened by the use of pad 10, while also promoting full recovery by preserving reliably sanitary conditions around the traumatized perineal region and providing targeted cooling via ice pouch 14 (shown in FIG. 1 and further described below).

The nominal dimensions of pad assembly 10, shown in FIG. 4, may be scaled up or down to accommodate different-sized patients. For example, the length L of perineal portion 26 may be as small as 8.0 inches, 8.5 inches or 9.0 inches, or as large as 9.5 inches, 10.0 inches or 11.0 inches, or may be any nominal value within any range defined by any pair of the foregoing values. The width W of dorsal portion 24 may be as small as 11.0 inches, 12.0 inches or 12.5 inches, or as large as 13.0 inches, 14.0 inches or 15.0 inches, or may be any nominal value within any range defined by any pair of the foregoing values. To preserve the equilateral T-shape described above, length L and width W may scale up or down together, provided these values retain a W:L ratio between 1.0 and 1.4. Similarly, the nominal width W2 of perineal portion 26 may be between 8.0 and 11.0 inches and the nominal length L2 of dorsal portion 24 may be between 6.5 and 9.5 inches, provided the W2:L2 ratio remains between 1.0 and 1.4.

Turning again generally to FIGS. 1-4, perineal portion 26 of pad assembly 10 also includes arcuate, convex medial and lateral edges 28. In particular, these arcuate edges 28 are provided in the perineal portions 36, 56 of outer and inner covers 12, 18 respectively. In the illustrated embodiment, each arcuate edge 28 defines a radius of about 13.0 inches, though this nominal value may scale up or down with the nominal size of pad 10 with nominal values ranging from 11.0 inches to 15.0 inches. Arcuate edges 28 follow the natural curvature of the perineal region of the body, and provide a secure yet comfortable fit that promotes fluid retention, cooperates with existing undergarments, and facilitates patient comfort and dignity. In an exemplary embodiment shown in FIGS. 3 and 4, arcuate edges 28 taper inwardly from the ventral edge of perineal portion 26 to a minimum nominal value about halfway along the ventral/dorsal extent of perineal portion 26, then taper back outwardly toward the junction with dorsal portion 24. As noted above, peripheral strip 38 maintains its even (i.e., 1.0 inch) width throughout this tapered portion. In the illustrated embodiment of FIG. 4, absorbent body 16 has a nominal medial/lateral width of about 6.0 inches at the ventral edge and at the dorsal junction with dorsal portion 24, tapering a minimum width of about 3.5 inches halfway along the ventral/dorsal extent of perineal portion 26.

Figure 2:
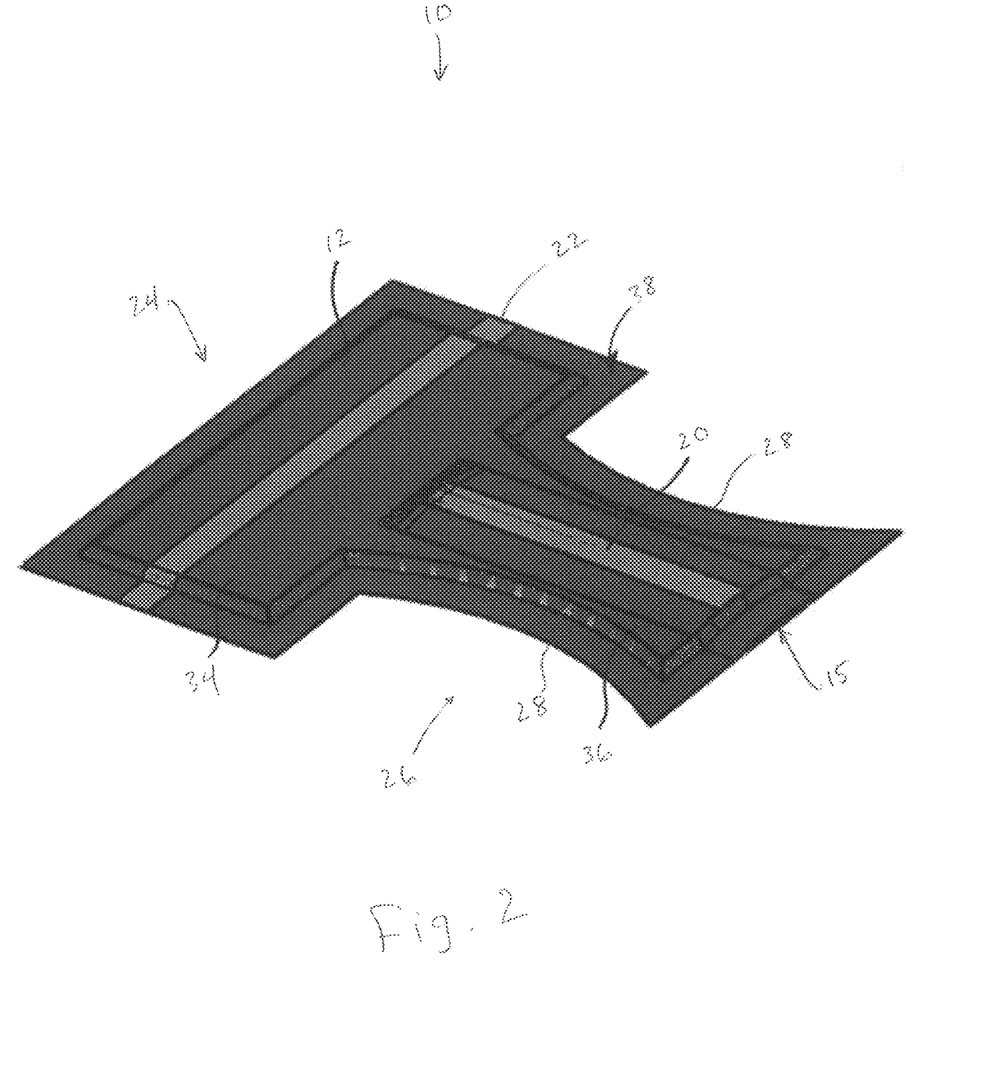
FIG. 2 is a perspective view of the pad assembly shown in FIG. 1.

As shown in FIG. 1 and noted above, pad assembly 10 includes ice pouch 14 disposed between perineal portion 36 of outer cover 12 and perineal portion 46 of absorbent body 16. Ice pouch 14 includes an opening 15 along its ventral edge, as shown in FIGS. 2 and 3, which is sized to accept ice chips from a typical ice machine found in many home and hospital settings. In an exemplary embodiment, opening 15 may be about 3.0 inches wide for compatibility with a typical crushed ice dispensing machine common in patient recovery wards. In particular, this 3-inch width allows ice pouch 14 to be filled directly from the dispenser of such a crushed ice dispensing machine.

As best shown in FIG. 3, ice pouch 14 has the same ventral/dorsal length L of perineal portion 26 (FIG. 4). Thus, when ice pouch 14 is filled with ice chips, targeted cooling is provided in the perineal region only, where trauma from childbirth, vasectomy, or other perineal injury is typical concentrated. Moreover, cooling from ice pouch 14 avoids the area covered by dorsal portion 24, where only absorbency is needed to absorb bodily fluids flowing backwardly from the perineal trauma in a supine patient. As noted above, perineal portion 26 may have varying lengths L depending on the overall size of perineal pad 10, and therefore ice pouch 14 may also have varying lengths L commensurate with perineal portion 26 and sized appropriately to the size of pad assembly 10. In addition, the overall width (along a medial/lateral direction) of ice pouch 14 may be the same as the width at opening 15, e.g., about 3 inches. In an exemplary embodiment, this width remains substantially constant throughout the ventral/dorsal length of ice pouch 14 to provide the targeted perineal cooling as noted above. Opening 15 may be releasably or permanently sealed to retain water from melted ice. For example, opening 15 may include a polymer zipper-type closure (e.g., of the sort found in reclosable plastic bags), or an adhesive-based closure, or any another other closure type as may be required or desired for a particular application.

Figure 6:
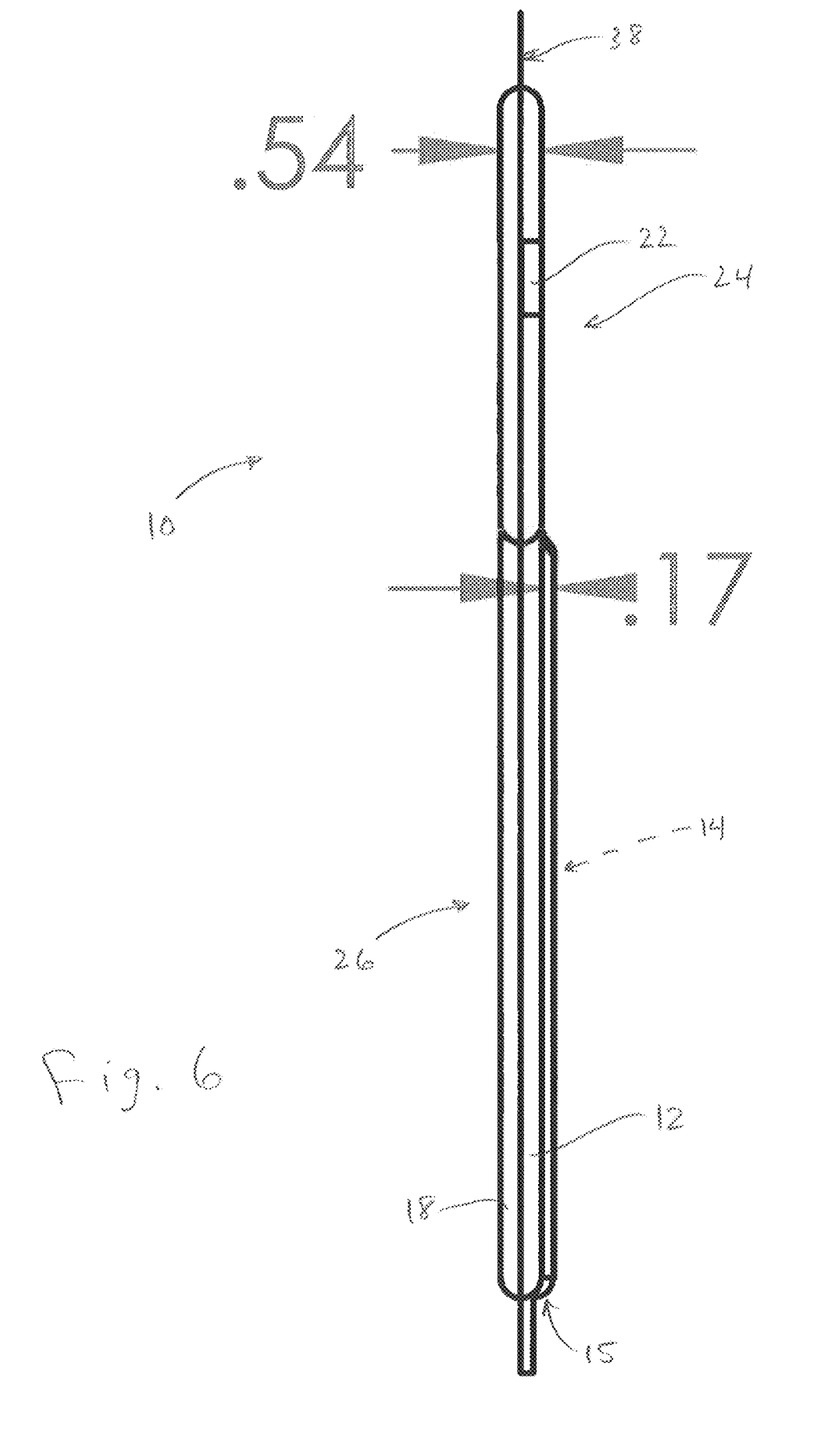
FIG. 6 is a side elevation view of the pad assembly shown in FIG. 1.

Turning now to FIG. 6, a side elevation view of pad assembly 10 illustrates that the thickness of dorsal portion 24 is about 0.54 inches, while the thickness of perineal portion 26 includes an additional 0.17 inches in thickness to accommodate ice pouch 14, for a total thickness of 0.71 inches. These thicknesses are small enough to facilitate patient comfort and compatibility with existing undergarments, while allowing enough interior space for the highly absorbent body 16. More particularly, the interior space between covers 12, 18 provides for lofted material which permits absorbent body 16 to absorb a relatively large quantity of bodily fluid. This large absorptive capacity minimizes the frequency of pad changes needed during patient recovery. Given that 15 liters of bodily fluids may be produced by a single patient over a 1.5- to 2-day recovery, the ability to absorb at least 100 milliliters per pad allows for pad changes only upon regular visits from a nurse or other caretaker.

Pad assembly 10 may also include adhesive strips 20 and 22, as best shown in FIG. 2. Adhesive strip 20 is disposed along the outer surface of perineal portion 26 and extends along a ventral/dorsal direction. Adhesive strip 22 is disposed along the outer surface of dorsal portion 24 and extends along a medial/lateral direction. Both adhesive strips 20, 22 include an outwardly-facing adhesive material configured to adhere to an undergarment, such that pad assembly 10 may be coupled or fixed to the undergarment prior to donning the undergarment in the usual fashion. In an exemplary embodiment, release strips may be adhered to adhesive strips 20, 22 for transport and storage of pad assemblies 10, and these release strips may be removed to expose the outwardly facing adhesive of adhesive strips 20, 22 immediately prior to application to an undergarment.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A perineal pad assembly comprising:
    an inner cover configured to transport a bodily fluid away from the skin of a patient;
    an outer cover impermeable to the bodily fluid,
    the inner cover and the outer cover cooperating to form a T-shape with a perineal portion extending along a ventral/dorsal direction and a dorsal portion extending along a medial/lateral direction; and
    an ice pouch disposed between the perineal portion of the outer cover and the perineal portion of the inner cover;
    wherein the ice pouch includes an opening disposed proximate a ventral edge of the of the perineal pad assembly, the opening sized to accept ice chips.

2. The perineal pad assembly of claim 1, wherein the ice pouch defines a ventral/dorsal length commensurate with a ventral/dorsal length of the perineal portion.

3. The perineal pad assembly of claim 2, wherein the ice pouch defines a medial/lateral width that is substantially constant throughout the ventral/dorsal length.

4. The perineal pad assembly of claim 3, wherein:
    a width of the opening and the medial/lateral width of the ice pouch are each about 3.0 inches; and
    the ventral/dorsal length of the ice pouch is between 8 and 11 inches.

5. The perineal pad assembly of claim 1, wherein the dorsal portion has a thickness of about 0.54 inches and the perineal portion has a thickness of about 0.71 inches.

6. A perineal pad assembly comprising:
an inner cover configured to wick a bodily fluid;
an outer cover impermeable to the bodily fluid,
the inner cover and the outer cover each forming a T-shape with a perineal portion extending along a ventral/dorsal direction and a dorsal portion extending along a medial/lateral direction;
an ice pouch disposed between the perineal portion of the outer cover and the perineal portion of the inner cover, the ice pouch including an opening disposed proximate a ventral edge of the of the perineal pad assembly, the opening sized to accept ice chips; and
an absorbent body formed from a highly absorbent material and disposed between the ice pouch and the inner cover, the absorbent body forming a T-shape commensurate with the T-shape formed by the inner and outer covers.

7. The perineal pad assembly of claim 6, wherein the absorbent body is configured to absorb at least 100 milliliters of fluid.

8. The perineal pad assembly of claim 7, further comprising:
a ventral/dorsal adhesive strip disposed along an outer surface of the perineal portion of the outer cover and configured to adhere to an undergarment; and
a medial/lateral adhesive strip disposed along an outer surface of the dorsal portion of the outer cover and configured to adhere to the undergarment.

9. The perineal pad assembly of claim 8, wherein:
the perineal portion of the inner cover and the outer cover defines a perineal portion length along the ventral/dorsal direction and a perineal portion width along the medial/lateral direction;
the dorsal portion of the inner cover and the outer cover defines a dorsal portion length along the ventral/dorsal direction and a dorsal portion width along the medial/lateral direction;
the perineal portion width is between 1.0 and 1.4 times the dorsal portion length; and
the dorsal portion width is between 1.0 and 1.4 times the perineal portion length,
whereby the perineal pad assembly defines a substantially equilateral T-shape.

10. A perineal pad assembly comprising:
an inner cover configured to transport a bodily fluid away from the skin of a patient;
an outer cover impermeable to the bodily fluid;
the inner cover and the outer cover cooperating to form a T-shape with a perineal portion extending along a ventral/dorsal direction and a dorsal portion extending along a medial/lateral direction;
an ice pouch disposed between the perineal portion of the outer cover and the perineal portion of the inner cover;
an absorbent body formed from a highly absorbent material and disposed between the ice pouch and the inner cover, the absorbent body forming a T-shape commensurate with the T-shape formed by the inner and outer covers; and
a peripheral strip enclosing the absorbent body within an interior pocket.

11. The perineal pad assembly of claim 10, wherein the peripheral strip defines a common width around a periphery of the perineal pad assembly.

12. The perineal pad assembly of claim 11, wherein the common width is about 1.0 inch.

13. A perineal pad assembly comprising:
an inner cover configured to transport a bodily fluid away from the skin of a patient;
an outer cover impermeable to the bodily fluid,
the inner cover and the outer cover cooperating to form a T-shape with a perineal portion extending along a ventral/dorsal direction and a dorsal portion extending along a medial/lateral direction; and
an ice pouch disposed between the perineal portion of the outer cover and the perineal portion of the inner cover, wherein:
the perineal portion of the inner cover and the outer cover defines a perineal portion length along the ventral/dorsal direction and a perineal portion width along the medial/lateral direction;
the dorsal portion of the inner cover and the outer cover defines a dorsal portion length along the ventral/dorsal direction and a dorsal portion width along the medial/lateral direction;
the perineal portion width is between 1.0 and 1.4 times the dorsal portion length; and
the dorsal portion width is between 1.0 and 1.4 times the perineal portion length,
whereby the perineal pad assembly defines a substantially equilateral T-shape.

14. The perineal pad assembly of claim 13, wherein:
the perineal portion length is between 8 and 11 inches; and
the dorsal portion width is between 11 and 15 inches.

15. The perineal pad assembly of claim 14, wherein:
the perineal portion width is between 8 and 11 inches; and
the dorsal portion length is between 6.5 and 9.5 inches.

16. A perineal pad assembly comprising:
an inner cover configured to transport a bodily fluid away from the skin of a patient;
an outer cover impermeable to the bodily fluid,
the inner cover and the outer cover cooperating to form a T-shape with a perineal portion extending along a ventral/dorsal direction and a dorsal portion extending along a medial/lateral direction; and
an ice pouch disposed between the perineal portion of the outer cover and the perineal portion of the inner cover;
wherein the perineal portion of the inner cover and the outer cover has arcuate, convex medial and lateral edges.

17. The perineal pad assembly of claim 16, wherein the convex medial and lateral edges each define a radius between 11 and 15 inches.

18. A perineal pad assembly comprising:
an inner cover configured to transport a bodily fluid away from the skin of a patient;
an outer cover impermeable to the bodily fluid,
the inner cover and the outer cover cooperating to form a T-shape with a perineal portion extending along a ventral/dorsal direction and a dorsal portion extending along a medial/lateral direction;
an ice pouch disposed between the perineal portion of the outer cover and the perineal portion of the inner cover;
a ventral/dorsal adhesive strip disposed along an outer surface of the perineal portion of the outer cover and configured to adhere to an undergarment; and
a medial/lateral adhesive strip disposed along an outer surface of the dorsal portion of the outer cover and configured to adhere to the undergarment.

* * * * *